United States Patent
Kulesza (10) Patent No.: US 10,092,491 B2
(45) Date of Patent: Oct. 9, 2018

(54) SKIN RENEWAL ENHANCER

(71) Applicant: John E. Kulesza, Berlin, CT (US)

(72) Inventor: John E. Kulesza, Berlin, CT (US)

( * ) Notice: Subject to any disclaimer, the term of this patent is extended or adjusted under 35 U.S.C. 154(b) by 137 days.

(21) Appl. No.: 15/075,924

(22) Filed: Mar. 21, 2016

(65) Prior Publication Data

US 2016/0271033 A1    Sep. 22, 2016

Related U.S. Application Data (60) Provisional application No. 62/135,743, filed on Mar. 20, 2015.

(51) Int. Cl.
| | | |
|---|---|---|
| *A61K 8/19* | (2006.01) | |
| *A61K 8/42* | (2006.01) | |
| *A61K 8/365* | (2006.01) | |
| *A61Q 19/08* | (2006.01) | |

(52) U.S. Cl.
CPC .............. *A61K 8/42* (2013.01); *A61K 8/19* (2013.01); *A61K 8/365* (2013.01); *A61Q 19/08* (2013.01); *A61K 2800/28* (2013.01); *A61K 2800/884* (2013.01)

(58) Field of Classification Search
CPC .... A61K 44/10; A61K 9/0014; A61K 31/403; A61K 31/4035; A61K 45/06; A61K 31/426; A61K 31/26; A61K 31/167; A61K 8/34; A61K 8/345; A61K 8/891; A61K 8/375
See application file for complete search history.

(56) References Cited

U.S. PATENT DOCUMENTS

| | | | | |
|---|---|---|---|---|
| 5,520,908 | A * | 5/1996 | Lundmark | ........... A61K 8/0295 424/70.1 |
| 2003/0104080 | A1* | 6/2003 | Singh | ........................ A61K 8/31 424/729 |
| 2014/0073613 | A1* | 3/2014 | Sundbom Nilsson | ...................... A61K 9/0014 514/162 |

* cited by examiner

*Primary Examiner* — Nannette Holloman
(74) *Attorney, Agent, or Firm* — Dinsmore & Shohl LLP (57) ABSTRACT

A system for enhancing skin renewal is provided, including a first phase having an anhydrous solvent, a hydroxy acid, and urea, and a second phase having a neutralizing agent and optional abrasive. A composition is provided, wherein the first phase includes glycerin, lactic acid, and urea, and wherein the second phase includes a neutralizing agent and optional abrasive. A process of increasing the rate of skin cell renewal in a subject is provided, which includes topically applying systems or compositions of the disclosure, such that dead skin cells are removed and replaced with new corneocytes, thereby increasing the rate of skin cell renewal.

15 Claims, 2 Drawing Sheets

SKIN RENEWAL ENHANCER

CROSS-REFERENCE TO RELATED APPLICATIONS

This application claims priority under 35 U.S.C. § 119(e) to U.S. Provisional Application Ser. No. 62/135,743, filed Mar. 20, 2015, which is incorporated by reference in its entirety.

FIELD

The disclosure relates to the prevention of skin aging. Generally, systems, compositions, and methods are provided that enhance skin cell turnover, reduce wrinkles, and improve appearance in a user while reducing skin irritancy observed with traditional chemical peel agents.

BACKGROUND

Animal skin serves essential roles in protecting an organism from environmental insults. Numerous specific skin functions include protection, excretion, secretion, absorption, thermoregulation, pigmentogenesis, accumulation, sensory perception, and regulation of immunological processes. The structural and chemical changes in the skin during aging reduce the effectiveness of skin to achieve each of these principal functions. Upon reaching the later stages of life, most previously robust skin functions are reduced, some by as much as 50-60%. The physiological changes associated with these reductions include impairment of the barrier function, decreased turnover of epidermal cells, reduced numbers of keratinocytes and fibroblasts, and a reduced vascular network particularly around hair bulbs and glands. A side effect of these changes is an increase in the appearance of skin wrinkles and previously unrecognized pigmented areas.

In an effort to prevent unwanted aging of skin or the appearance of aged skin, many people use chemical peels to reduce wrinkles and increase skin cell renewal. Normal skin represents a balanced cell renewal system where fully differentiated corneocytes are continually shed and replaced by new cells generated at lower skin levels. Normally this process occurs at a steady state whereby the new cells are produced at rates equivalent to the shedding of surface cells. Chemical peels offer a way to increase this rate of skin renewal. Peels function by actively removing damaged outer layers of skin, replacing it with new, more hydrated, and more robust skin cells. This improves the smoothness of skin, reducing wrinkles, and providing a younger appearance. Chemical peels are also beneficial for those with facial blemishes such as acne scarring, anomalous pigmentations, or for removing actinic keratoses.

Chemical peels are available in several formulations that provide superficial, moderate, or deep peels. Irritancy is a hallmark of all chemical peels, and all peels induce irritancy in the skin of a subject, even superficial peels. Traditionally, this irritancy is a source of the peeling nature of the compositions.

Superficial chemical peels typically remove only the upper corneous layer of the epidermis. Peeling agents include alpha-hydroxy acids including citric acid (e.g. citrus-derived), glycolic (derived from sugar cane), lactic acid (derived from milk), malic acid (derived from apples) and tartaric acid (derived from grapes). These are the mildest of agents yet produce extreme irritancy such as stinging, redness, dryness, and other skin irritation. Typically only mild skin smoothing or acne improvements are observed with this level of chemical peel.

Moderate depth chemical peels penetrate into the upper layers of the dermis causing more aggressing sloughing of the outer skin cell layers. Typical agents for moderate peels include higher concentration hydroxy acids and trichloroacetic acid at concentrations of 20-50%. The greater the concentration of the peeling agent, the deeper the peel. Moderate peels function to smooth fine surface wrinkles, surface blemishes to the skin, and unwanted pigmentation. The irritation to the skin is much greater than a superficial peel and recovery times and precautions are also increased.

The deep peel, commonly achieved by applications of phenol, is used to treat deep wrinkling, remove deeper pigmentation anomalies, and treat precancerous skin growths. Phenol peels contain highly irritating ingredients that can have long lasting affects on skin appearance. Phenol peels can leave the skin with a lighter pigmentation and damage the skin cells such that new pigment production cannot occur. Recovery from phenol peels can be several months and may require permanent avoidance of sun exposure.

The ubiquitous irritating nature of prior skin renewal enhancing compositions is inherent to the compositions, previously thought essential for function and the primary source of unwanted side effects of treatment. Thus, there exists a need for compositions, systems, and methods of enhancing skin renewal while reducing irritancy.

SUMMARY

The following summary is provided to facilitate an understanding of some of the innovative features unique to the present disclosure and is not intended to be a full description. A full appreciation of the various aspects of the disclosure can be gained by taking the entire specification, claims, drawings, and abstract as a whole.

Accordingly, systems, compositions, and methods for enhancing skin renewal are provided herein. In one aspect, systems for enhancing skin renewal are provided, an exemplary system including: (a) a first phase including (i) an anhydrous solvent, (ii) a hydroxy acid, and (iii) urea; and (b) a second phase including a neutralizing agent.

In other aspects, processes of increasing a rate of skin renewal in a subject are provided, an exemplary process including: (a) topically applying a first phase of a system to a skin treatment area of the subject for a treatment time, wherein the first phase includes an anhydrous solvent, a hydroxy acid, and urea; and (b) topically applying a second phase of a system to the skin treatment area of the subject for a neutralizing time, wherein the second phase comprises a neutralizing agent; whereby a naturally occurring outer layer of dead skin cells of the skin treatment area is removed and replaced with new corneocytes, thereby increasing a rate of skin renewal.

In other aspects, compositions for enhancing skin renewal are provided, exemplary compositions including: (a) a first phase including: (i) glycerin, (ii) lactic acid, and (iii) urea; and (b) a second phase including (i) triethanolamine, and (ii) hydrated silica beads; wherein the first phase and the second phase are intermixed upon topical application to a skin treatment surface.

These and other objects, features, aspects, and advantages will become apparent to those of ordinary skill in the art from a reading of the following detailed description and the appended claims.

DETAILED DESCRIPTION

The following description of particular aspect(s) is merely exemplary in nature and is in no way intended to limit the scope of the disclosure, its application, or uses, which may, of course, vary. The disclosure is presented with relation to the non-limiting definitions and terminology included herein. These definitions and terminology are not designed to function as a limitation on the scope or practice of the disclosure but are presented for illustrative and descriptive purposes only. While the processes and devices are described as an order of individual steps or using specific arrangements of elements, it is appreciated that described steps or elements may be interchangeable such that the description includes multiple parts or steps arranged in many ways as is readily appreciated by one of skill in the art.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, or percentage is meant to encompass variations of in some aspects ±20%, in some aspects ±10%, in some aspects ±5%, in some aspects ±1%, in some aspects ±0.5%, and in some aspects ±0.1% from the specified amount, as such variations are appropriate practice the disclosed subject matter.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Provided are systems, compositions, and processes having utility for enhancing skin renewal with greatly reduced irritancy relative to traditional chemical peel agents, systems, and compositions. A system and composition includes two phases, with a first phase acting as a moisturizing and keratolytic phase, and an optional second phase acting as a neutralizing and optionally abrasive phase. A first moisturizing and keratolytic phase includes a substantially anhydrous (less than or equal to 4% or less than or equal to 1% water) solvent, a hydroxy acid, and urea. A second phase includes a neutralizing agent suitable for neutralizing the hydroxy acid and optionally an abrasive agent in the form of particles. The resulting topical composition and system is suitable for application to skin, optionally human skin, optionally for the treatment or prevention of wrinkles, dry skin, dermatoses, acne, keratoses, photo-aging, melasma, pseudofolliculitis barbae (razor bumps) and other skin conditions treatable by increased skin cell renewal. In a system, a first phase and a second phase are optionally present in independent containers that are packaged or otherwise associated for concomitant use.

TCA is commonly used for chemical peels due to its ability to affect skin turnover rates. The concentration of TCA in chemical peels is typically 20% or greater owing to the high level of irritancy of TCA as well as its lack of stability at low concentrations. The high level of irritancy observed at concentrations less than 20% historically made TCA inappropriate for superficial skin peels or general topical application. The compositions and systems provided herein include active agents such as hydroxy acids that are much more desirable than TCA because of the greatly reduced irritancy associated with these compounds due to their moisturizing capabilities. However, hydroxy acids such as lactic acid as used in traditional chemical peels are combined with water to produce a "controlled burn" that results in the epidermolysis and the peeling effect. Contrary to prior methods, the present systems, compositions, and processes are provided with the actives in anhydrous, polar solvents.

It was unexpectedly discovered that both hydroxy acids and urea can be fully solubilized in anhydrous solvent at concentrations suitable for use as a chemical peel. Illustratively, for a peeling activity in the provided compositions and systems the hydroxy acid and urea must be present at a concentration of 8-10% or greater, with much greater efficacy at 10% or greater. It was discovered that anhydrous polar solvents can fully solubilize (i.e. no observable haze at 25° C.) both hydroxy acids and urea up to concentrations of 25%, thereby allowing significant efficacy when applied to the skin. The use of anhydrous glycerin (as one example) alone or optionally with or substituted by other anhydrous polar solvents (e.g. anhydrous polar solvents such as propylene glycol, butylene glycol, dimethylisosorbide, etc.) allows for the elimination of water and the prevention of the "burn" experienced in prior systems.

In the art, peeling agents are commonly applied to or removed from the skin using water or are provided in aqueous solutions (greater than 2% water) previously thought necessary to solubilize the actives. The processes, compositions, and systems provided herein optionally exclude water with the hydroxy acid phase, thereby preventing the burn experienced by water ionizing the hydroxy acid, either in the composition or at the site of application. A second phase includes a neutralizing agent suitable for neutralizing the hydroxy acid such that an aqueous or partially aqueous removal system (e.g. wet towel) may be used to remove the first and second phases of the system from the skin without additional unwanted irritation or stinging.

Systems and Compositions for Enhancing Skin Renewal

A system for enhancing skin renewal includes a first phase acting as a moisturizing and keratolytic material. A moisturizing and keratolytic material optionally includes a hydroxy acid and urea. A hydroxy acid is optionally an alpha, beta, or gamma hydroxy acid. Illustrative examples of alpha hydroxy acid include glycolic acid, lactic acid, malic acid, citric acid. Examples of beta hydroxy acids include salicylic acid, acetylsalicylic acid, and the like. In particular aspects, a hydroxy acid is lactic acid, optionally alone or combined another hydroxy acid. Optionally, lactic acid is the sole hydroxy acid.

A first phase also includes urea. Urea is used in the first phase as a peeling agent that works in conjunction and synergistically with the hydroxy acid, particularly lactic acid.

The first phase includes an anhydrous solvent optionally as a predominant, optionally glycerin. Sources of glycerin are known in the art, such as Dow Chemical Co. Glycerin operable herein is optionally anhydrous, such that the glycerin contains less than 5 percent by weight moisture. Optionally, glycerin is a 96% USP glycerin. Optionally, glycerin is a 99.5% USP glycerin. In some aspects, the glycerin is dehydrated such as by vacuum distillation or pervaperation as described by Khairnar and Pangarkar, *J. Am. Oil Chem. Soc.,* 2004; 81:505-10.

In the first phase the hydroxy acid and urea are each present at a concentration of from 8% by weight to 25% by weight. It is specifically appreciated that any value or range between 8% by weight to 25% by weight of either or both of the hydroxy acid and urea are envisioned as part of the disclosure. Optionally, the hydroxy acid and urea are each present at concentrations from 10% by weight to 20% by weight and not exceeding 20% by weight. Optionally, the hydroxy acid and urea are each present at concentrations from 10% by weight to 18% by weight. Optionally, the hydroxy acid and urea are each present at concentrations from 15% by weight to 20% by weight. Optionally, the hydroxy acid and urea are each present at concentrations of 20% by weight. Optionally, the hydroxy acid and urea each do not exceed concentrations of 20% by weight.

In some aspects, a hydroxy acid or other peel agent with no moisturizing capability is absent from either a first phase or second phase material. Such materials that are optionally excluded include but are not limited to glycolic acid, salicylic acid or trichloroacetic acid.

The relative ratio of the hydroxy acid to urea was also unexpectedly discovered to be essential to the function of the system and compositions with reduced or eliminated burn and to function with a second phase material. The ratio of hydroxy acid to urea is optionally in the range of 2:1 to 1:2, with unexpectedly superior results at a ratio of 1:1, optionally ±10%.

A system further includes a second phase that acts as a neutralizing and optionally abrasive phase. A second phase includes one or more neutralizing agents. Illustrative examples of neutralizing agents include sodium hydroxide, potassium hydroxide, triethanolamine, ammonium hydroxide, and tris(2-aminoethyl)amine sold by Dow Chemical as TRIS AMINO.

A second phase optionally includes an abrasive agent. An abrasive agent is a solid particulate material. An abrasive agent is a physiologically-acceptable abrasive. Illustrative examples of such abrasives include polyethylene granules and silica particles, optionally hydrated silica particles. An abrasive optionally has a particle size ranging from about 60 to 200 microns. An exemplary abrasive is hydrated silica particles in the 60 to 200 micron range, sold under the brand name SILICAMI by Alban Muller International. In certain aspects, an abrasive is present in an amount of 1-50% by weight, optionally 1-10% by weight, optionally 1-5% by weight. In some aspects, 1, 2, 3, 4, or more different abrasives are included.

A composition or system as provided herein optionally includes one or more anti-irritants alone or as a portion of a first phase, a second phase, or both. An anti-irritant is any molecule or combination of molecules, naturally derived or synthetic, that will reduce or prevent irritation to the skin of a subject. In some aspects an anti-irritant is naturally derived, such as a plant extract, or plant or animal derived molecule. Optionally, an anti-irritant is synthetic and derived from a non-natural source. In some aspects, an anti-irritant is derived from a combination of sources, optionally natural and synthetic. One specific example of a family of anti-irritants are the indolequinazoline alkaloids.

An anti-irritant is optionally present in a composition or system in an amount ranging from 0.1% to 5% by weight, or any value or range therebetween. Optionally, an anti-irritant is present in an amount from 0.5% to 3%. In some aspects, an anti-irritant is present at 0.5%, 0.75%, 1.0%, 1.5%, or 2% by weight. It is appreciated that more than 5% by weight of a composition, system or phase thereof may be an anti-irritant.

Illustrative examples of anti-irritants include: plant extracts; plant oils; lipids such as ceramides, fatty acids, and fatty alcohols; and steroids such as cholesterol. Illustrative examples of anti-irritants are plant oils, illustratively lemon oil. Other plant oils may be included in a composition or system illustratively including agar oil, ajwain oil, *angelica* root oil, anise oil, balsam oil, basil oil, bergamot oil, black pepper essential oil, buchu oil, *cannabis* flower essential oil, caraway oil, cardamom seed oil, carrot seed oil, castor oil, cedarwood oil, chamomile oil, cinnamon oil, cistus, citronella oil, clary sage, clove leaf oil, coriander, costmary oil, cranberry seed oil, cumin oil/black seed oil, cypress, davana oil, dill oil, *eucalyptus* oil, fennel seed oil, fenugreek oil, frankincense oil, *galbanum*, geranium oil, ginger oil, grapefruit oil, grape seed oil (e.g. *Vitis vinifera*), henna oil, jasmine oil, juniper berry oil, lavender oil, lemon oil, lemongrass oil, *litsea cubeba* oil, melissa oil (Lemon balm), *mentha arvensis* oil/mint oil, mugwort oil, mustard oil, myrrh oil, neroli oil, orange oil, oregano oil, orris oil, parsley oil, patchouli oil, *perilla* essential oil, pennyroyal oil, peppermint oil, pine oil, rose oil, rosehip oil, rosemary oil, rosewood oil, *sassafras* oil, savory oil, schisandra oil, spearmint oil, star anise oil, tarragon oil, tea tree oil, thyme oil, vetiver oil, yarrow oil and ylang-ylang oil.

Methods of producing plant oils are known in the art illustratively by oil extraction or by pressing the seeds of a plant such as grape seeds, peanut seeds, or other seed. Many plant oils are available in the market and a person of ordinary skill in the art recognizes where to obtain them.

Methods of producing plant extracts are known in the art and illustratively include grinding of plant material and extraction in water, ethanol, or combinations thereof. To improve the extract quality, an extraction is optionally performed with heating to between 50° C. to 100° C. Extracted material is optionally filtered one or more times prior to evaporation of extraction solvent. It is appreciated that other methods of preparing plant extracts are known in the art and applicable to the preparation of one or more plant extracts useful in the compositions or systems provided herein.

Other specific illustrative examples of anti-irritants include licorice and its extracts, dipotassium glycyrrhizinate, oat and oat extracts, candelilla wax, alpha bisabolol, aloe vera, Manjistha (extracted from plants in the genus *Rubia*, particularly *Rubia cordifolial*), and Guggal (extracted from plants in the genus *Commiphora*, particularly *Commiphora Mukul*). It is appreciated that more than one anti-irritant may be included in a composition or system. In some aspects, EVODIOX (*Evodia rutacarpa* fruit extract, butylated hydroxy toluene, butylene glycol; CAS #138-37-0; 107-88-0) Barnet Products Corp., Englewood Cliffs, N.J.) is included along with a second, third, or additional anti-irritant.

A composition or system optionally includes one or more bioactive agents. A "bioactive agent" is a chemical or biological molecule or combination of molecules suitable for delivery to the skin of a subject and will impart some observable change to the skin or underlying layers either alone or when in combination with other materials. Optionally, an active agent has pharmaceutical activity and is present for the treatment or prevention of a skin condition. A bioactive agent optionally has activity that is: anti-inflammatory; anti-bacterial; anti-parasitic; anti-viral; analgesic; immunity modulating and/or stress relaxing; altering of cell growth or death; promoting apoptosis; inducing alterations in DNA such as alkylation, oxidation, or base hydrolysis; inhibitory or stimulatory of enzyme activity; or combinations thereof.

Bioactive agents include but are not limited to active herbal extracts; acaricides; age spot and keratose removing agents; allergens; analgesics; local anesthetics; antiacne agents; antiallergic agents; antiaging agents; antibacterials; antibiotics; antiburn agents; antineoplastic and/or ophthalmic agents illustratively including 5-fluorouracil, doxorubicin, imiquimod, and sodium [o-(2,6-dichloranilino) phenyl] acetate; antidandruff agents; antidepressants; antidermatitis agents; antiedemics; antihistamines; antihelminths; antihyperkeratolyte agents; antiinflammatory agents such as steroidal or non-steroidal anti-inflammatory agents illustratively flurbiprofen, ibuprofen, naproxen, indomethacin, glucocorticoids such as hydrocortisone, and other anti-inflammatory compounds; antilipemics; antimicrobials such as azelaic acid, erythromycin, sodium sulfacetamide, tetracycline and derivatives, and clindamycin; anti-mitotic drugs illustratively colchicine taxol and related compounds; antiproliferative agents; antioxidants; anti-wrinkle agents; antipruritics; antipsoriatic agents; antirosacea agents; antiseborrheic agents; antiseptics; antiswelling agents; antiviral agents illustratively ganciclovir, trifluorothymidine and related compounds; antiyeast agents; astringents; aromatic molecules such as benzoyl peroxide, resorcinol, hydroquinone; topical cardiovascular agents; chemotherapeutic agents; corticosteroids; dicarboxylic acids; disinfectants; fungicides; hair growth regulators; skin growth factors illustratively TGFα, epidermal growth factor, platelet derived growth factor, granulocyte macrophage colony stimulating factor (GM-CSF), interleukins, and others typically used for dermatological therapies; hormones; hydroxy acids; immunomodulators such as immunosuppressants and immunoregulating agents; insecticides; insect repellents; keratolytic agents; lactams; metals; metal oxides; miticides; neuropeptides; non-steroidal anti-inflammatory agents; oxidizing agents; pediculicides; photodynamic therapy agents; sanatives; scabicides; self tanning agents; skin whitening agents; vasoconstrictors; vasodilators; vitamins such as vitamin A or its derivatives, or vitamin D or its derivatives, or vitamin E or its derivatives; wound healing agents; wart removers; drugs that act on actin polymerization illustratively phalloidin, cytoclasin B and related compounds; inhibitors of dihydropyrimidine dehydrogenase (DPD), thymidine phosphorylase (TP) and/or uridine phosphorylase (UP) enzyme inhibitors; ultraviolet light (UV) filters illustratively benzophenone derivatives such as oxybenzone, octocrylene, octyl methoxycinnamate, and avobenzone; radiation proactive agents illustratively methyluracils such as 6-methyluracil and 4-methyluracil; and immunomodulating molecules such as tacrolimus, and pimecrolimus. As is known to one of skill in the art, in some instances a specific bioactive agent may have more than one activity, function or effect.

Optionally, a bioactive agent is vitamin A or its derivatives. Examples of vitamin A or its derivatives illustratively include retinoids such as retinal, retinoic acid, retinyl ester, retinol, tretinoin, isotretinoin, adapalene, tazarotene, and the like. In some aspects a vitamin A or its derivatives are present at between 0.001 to 2 weight percent.

A bioactive agent is optionally vitamin E or its derivatives. Illustrative derivatives of vitamin E include sodium vitamin E phosphate, lauryl imino dipropionic acid tocopheryl phosphate, tocopheryl glucoside, tocopheryl succinate, tocophersolan (tocopheryl polyethylene glycol 1000 succinate), tocophereth-5, tocophereth-10, tocophereth-12, tocophereth-18, or tocophereth-50. Vitamin E or its derivatives are optionally present in an amount ranging from 0.1% to 10% by weight, or any value or range therebetween. The use of vitamin E or its derivatives to increase exfoliation are illustrated in U.S. Pat. No. 6,645,514.

Numerous skin or systemic conditions are treatable with the system or composition as provided herein illustratively including acne, wrinkles, dryness, eczema, psoriasis, actinic and nonactinic keratoses, rosaceous, among others.

Optionally, a bioactive agent is present in less than 30 weight percent amounts. Optionally, a bioactive agent is present at a weight percent of 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.1, 0.01, 0.001, 0.0001, and any level in between or any range therein. Optionally, a bioactive agent is present at 20 percent by weight.

In some aspects, the bioactive agent is an anti-infective agent. Illustrative examples of an anti-infective agent include an antibiotic agent, an antibacterial agent, an antifungal agent, an agent that controls yeast, an antiviral agent and an antiparasitic agent. Exemplary anti-infective agents are beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that releases free radicals and/or active oxygen, a cationic antimicrobial agent, a quaternary ammonium compound, a biguanide, chlorohexidine, a triguanide, a bisbiguanide, a polymeric biguanide and a naturally occurring antibiotic compound, as well as analogs, derivatives, salts, ions, and complexes thereof.

A composition or system optionally includes one or more additives. It is appreciated, however, that a composition or system is optionally free of an additive. An additive illustratively is one or more antioxidants, anti-static agents, bulking agents, chelating agents, cleansers, colorants, conditioners, deodorants, diluents, dyes, emollients, flavonoids, fragrances, hair conditioners, humectants, ionization agents, moisturizers, occlusive agents, perfuming agents, pearlescent aids, perfuming agents, permeation enhancers, preservatives, protectants, skin penetration enhancers, softeners, solubilizers, sunscreens, sun blocking agents, sunless tanning agents, viscosity modifiers and vitamins. The source and type of additive operable herein is readily understood by one of skill in the art. Illustrative examples of additives are found in WO 2009/090558 and references cited therein, each of which is incorporated herein by reference.

A humectant, when included in a composition or system, helps retain moisture and also prevents rapid evaporation. As such, a humectant optionally does not include glycerin. Illustrative examples of humectants include ethoxydiglycol, benzyl alcohol, ethylene glycol, propylene glycol and propylene glycol derivatives, guanidine, aloe vera, aloe vera gel, allantoin, urazole, alkoxylated glucose, hyaluronic acid, salts of hyaluronic acid, lactamide monoethanolamine, panthanol, sorbitol, acetamide monoethanolamine and derivatives, esters, salts and mixtures thereof, as well as any suitable humectant found in Handbook of Pharmaceutical Additives published by Gower where one of ordinary skill in the art will recognize suitable humectants contained therein.

Some aspects of a composition or system include one or more additional moisturizers. Examples of additional moisturizers include allantoin, petrolatum, niacinamide, sodium PCA, shea butter, caprylic/capric/stearic triglyceride, candelilla wax, lanolin, hydrogenated oils, squalene, sodium hyaluronate and lysine PCA. Other examples may be found in the Handbook of Pharmaceutical Additives published by Gower.

Additional additives to benefit skin and its condition include ceramides, glycoceramides, pseudoceramides, sphingolipids such as sphingomyelins, cerebrosides, sulphatides, and ganglioside, sphingosines, dihydrosphingosine, phytosphingosines, and phospholipids. Illustrative examples of ceramides and glycoceramides include those described in U.S. Pat. Nos. 5,589,178, 5,661,118, and 5,688,752, each of which is incorporated by reference. Illustrative examples of pseudoceramides include those described in U.S. Pat. Nos. 5,198,210; 5,206,020; and 5,415,855, each of which is incorporated by reference.

A composition or system is optionally provided as a lotion, cream, gel, bar, ointment, or in impregnated pad form, optionally where a liquid is supplied separately from a pad but applied thereto prior to application to the skin. Optionally, the composition or system is provided in a single use container, the contents of which are applied directly to the stratum corneum of a subject or applied to an applicator pad for subsequent delivery to the subject.

Methods of Increasing the Rate of Skin Cell Renewal

Also provided are processes of increasing a rate of skin cell renewal in a subject. Skin cell renewal is defined as replacement of a naturally occurring outer layer of dead skin cells with new corneocytes in a stratum corneum. As such, skin cell renewal is distinguishable simply removing the outer layers of skin cells as the process requires maturation of underlying basal cells to outer layer corneocytes. A skin renewal process as it naturally occurs (keratinization) includes movement of basal cells outward from the basal layer, passing through the spinous and granular layers, and eventually becoming corneocytes located in the stratum corneum. The stratum corneum includes approximately 14 layers of dead cells and represents the outer layer of skin cells normally exposed to the environment. Approximately 14 days are normally required in human skin for the basal cells to move from the basal layer to the end of the granular layer and to become corneocytes, and another 14 days for the corneocytes to reach the outermost layer of the stratum corneum. As such, the overall natural skin cell renewal process takes approximately 28 days. Skin cell renewal rates are increased by the compositions, systems, and methods presently disclosed from 1% to 150% or more, optionally in excess of 10%, 20%, 30%, 40%, 50%, 60%, 70%, or 80%.

A process of increasing the rate of skin cell renewal illustratively includes applying a system or composition in two phases as described herein to a skin treatment area of a subject. A composition applied to the skin of a subject includes a first phase that includes at least an anhydrous solvent (illustratively, glycerin), hydroxy acid (illustratively, lactic acid), and urea. The first phase is applied to the skin of a subject by wiping, spraying, rubbing, or other traditional method of applying materials to the skin. A first phase is optionally applied in an even layer and allowed to remain in direct contact with the skin for a treatment time. A treatment time is optionally any time ranging from 1 minute to 30 minutes, or any value or range therebetween, optionally 10 to 20 minutes. In some aspects, a barrier is optionally applied on top of the first phase material to increase the penetration and subsequent peeling effects of the first phase material, or to decrease evaporation. A barrier is optionally any barrier that will reduce evaporation, air penetration, light penetration, heat penetration, or other to the skin. Optionally a barrier is one or more plastic films, strips, or other shapes.

Following the treatment time, a second phase material is applied on top of the first phase material, such that the first phase and the second phase intermix on the skin treatment surface. A second phase material includes at least a neutralizing agent. The second phase is optionally massaged into the skin for a neutralization time. A neutralization time is optionally about 1 to 10 minutes or any value or range therebetween, optionally 2-3 minutes. Optionally the massaging into the skin is continued until the skin color becomes visibly pinker or redder than prior to the application of the second phase material. In aspects that include an abrasive agent, the massaging will move the abrasive agent over the skin to promote removal of the upper, detached portion of the stratum corneum.

In some aspects, a process further includes a removal step, whereby any remaining or residual first phase and second phase material is removed from the skin treatment area. Optionally, a wiping apparatus such as a soft tissue or towel is used in a wiping action to remove the first phase and second phase materials. A wiping apparatus is optionally saturated or partially saturated with water to assist in the removal process. The wiping is optionally continued until all or substantially all of the abrasive particles, if present, are removed. The result of the process is a more youthful, smooth, hydrated appearance. It also minimizes prolonged skin dryness and peeling characteristic of more traditional chemical peels made from non-moisturizing keratolytic agents such as glycolic acid, salicylic acid and trichloroacetic acid.

As used herein the term "subject" refers to a human, non-human primate, pig, bovine, equine, mouse, rat, guinea pig, rabbit, hamster, or other mammal.

Application of a composition or system is optionally topical application. A composition is optionally topically applied at least one time, and optionally more than one time, where the application may be once daily, twice daily, once weekly, twice weekly, or other treatment regime as required to promote the desired outcome and dependent on the subject's underlying skin condition prior to treatment. The compositions or systems are optionally applied weekly, biweekly, or monthly. In some aspects, a single application of a composition or system is sufficient to induce increased skin cell renewal in a subject. Typical treatment periods include anywhere from one day or one week to 20 weeks or more. It is appreciated that, unlike prior compositions for topical application, the systems and compositions provided herein are suitable for continued use. Continued use is use for an indefinite period of time without interruption. Uninterrupted use (i.e. repeated applications at the same or substantially the same frequency) is possible with the compositions and systems provided herein. As such, a process optionally includes uninterrupted use for a treatment period. A treatment period as used herein is optionally from one day to 20 weeks or more, including any range therebetween. A treatment period is optionally indefinite. It is appreciated that while an increase in the rate of skin cell turnover may be observed after as little as a single application, improved results are observed after continued application for a period of time.

The compositions and systems formulated as described herein are optionally topically applied to the skin for the purposes of increasing the rate of skin cell renewal. A composition is optionally applied in the areas where fine lines, wrinkles, dry or inelastic skin or large pores are observed. Optionally, an additional or external moisturizer is applied with or after application of the compositions or systems to enhance the tactile comfort associated with application of the compositions and systems or to enhance wrinkle effacement and other benefits achieved by the compositions and systems. An improved characteristic of the composition and system is that the use of additional moisturizers or compositions to reduce the normally observed irritancy of prior chemical peel compositions is not required. As such, a composition or system optionally excludes a moisturizer, or a process excludes application of a moisturizer following application of a composition or system.

In some aspects, a process includes applying more than one composition or system of the formulations described herein to the skin of a subject. A second composition or system is optionally applied simultaneous with, or sequential to a first composition or system. It is appreciated that a third, fourth, or additional composition or system is optionally applied simultaneous with or sequential to another composition or system. A first composition or system and one or more additional compositions or systems optionally differ by the concentration of one or more actives or neutralizing agents present. A first period and a second or additional period are optionally 1 week to 20 weeks or more, or any value or range therebetween. A second period is optionally indefinite. Multiple periods are optionally separated by a rest period. A rest period is optionally one to 30 days or more. A rest period may improve the long term benefit of the applications, as it prevents a subject from acclimating to the treatment providing improved results in less overall time.

Also provided are processes of effacing wrinkles in the skin of a subject. Wrinkle effacement is achieved by applying a composition or system of a formulation described herein to the skin of a subject by the above treatment process for a period and thereby effacing the wrinkled appearance of the skin. A composition as formulated herein not only causes increases in skin cell turnover, but also, and optionally in the absence of traditionally known anti-wrinkle agents, effaces wrinkles on the skin to which the composition is applied. As such, the modes of administration, periods, and amounts of and elements of a composition of a formulation described herein used for increasing the rates of skin cell turnover are operable to efface wrinkles on the skin of a subject.

Various aspects of the present invention are illustrated by the following non-limiting examples. The examples are for illustrative purposes and are not a limitation on any practice of the present invention. It will be understood that variations and modifications can be made without departing from the spirit and scope of the disclosure. Reagents used are known to those of skill in the art who understand from which sources such agents may be obtained or how such reagents are synthesized from commercially available materials.

The following examples are given by way of illustration and are in no way intended to limit the scope of the present invention.

EXAMPLES

Example 1

Formulating a first phase composition.

Compositions including lactic acid and urea at varying concentrations of between 10% to 25% by weight are prepared similarly. All percentages are final first phase composition weight percent. For formation of first phase material that includes a 20% lactic acid and 20% urea in a 1:1 ratio of the solvent glycerin (Formula A), a actives are solvated in anhydrous glycerin warmed to a maximum of 40° C. to create a uniform solution optionally with vigorous mixing using a propeller mixer.

A first phase of formula A was made with the following ingredients in proportions as illustrated in Table 1:

TABLE 1

First phase formula A

| Ingredient | Amount in weight percent of the phase formulation |
|---|---|
| Glycerin (99% USP) | q.s. to 100% |
| Lactic acid (96% USP) | 20 |
| Urea USP | 20 |
| N-acetylcysteine | 5 |
| Benzyl alcohol NF | 1 |
| PEG-40 hydrogenated castor oil | 2 |

A second phase is formulated by combining the ingredients and gentle mixing as in Table 2.

TABLE 2

Second phase formulation A

| Ingredient | Amount in weight percent of the phase formulation |
|---|---|
| Deionized water | qs to 100% |
| polyethylene glycol 400 | 12 |
| hydrated silica beads | 3.2 |
| triethanolamine NF | 1.2 |
| dimethicone copolyol | 1 |
| hydroxyethyl cellulose | 0.5 |
| benzyl alcohol NF | 0.4 |

Additional formulations of a first phase are created by the same methods, including concentrations of lactic acid and urea varying between 10% and 25% by weight, as illustrated in Table 3.

TABLE 3

| Formula | Lactic acid (% w/w) | Urea (% w/w) |
|---|---|---|
| B | 10 | 10 |
| C | 15 | 15 |
| D | 25 | 25 |
| E | 10 | 15 |
| F | 10 | 20 |

TABLE 3-continued

| Formula | Lactic acid (% w/w) | Urea (% w/w) |
|---|---|---|
| G | 10 | 25 |
| H | 15 | 10 |
| I | 15 | 20 |
| J | 15 | 25 |
| K | 20 | 10 |
| L | 20 | 15 |
| M | 20 | 25 |
| N | 25 | 10 |
| O | 25 | 15 |
| P | 25 | 20 |

All reagents taught herein are obtainable from standard commercial chemical suppliers known to those of skill in the art, illustratively, Sigma-Aldrich, St. Louis, Mo.

Formulations B-P are formulated as formula A.

Example 2

Enhanced skin cell renewal by compositions. A second set of systems are produced by the same methods of Example 1 with 5% wt to 30% wt lactic acid and urea at various combinations in the background of the other ingredients in the phase 1 and phase 2 components of Example 1. The systems are tested for their ability to enhance skin cell turnover relative to saline (control) by the methods of Smith, W P, Cosmetics and Toiletries, 1994; 109:41-48. Briefly, the dansyl chloride method is used where dansyl chloride that is milled into petrolatum USP at 5% is applied under an occlusive patch to forearms for a period of 24 hours. Staining of skin cells is measured by quartz mineral lamp. The tested systems are applied to the test sites once per day (evening). The reduction in staining is monitored by daily measurements under quartz lamp.

Subjects are also measured for exfoliation rate by a forced exfoliation method. Briefly, skin squames are collected by adherence to a tape coated microscope slide pressed into the skin surface and quickly removed. The number of cells is measured by opacity.

Figure 1:
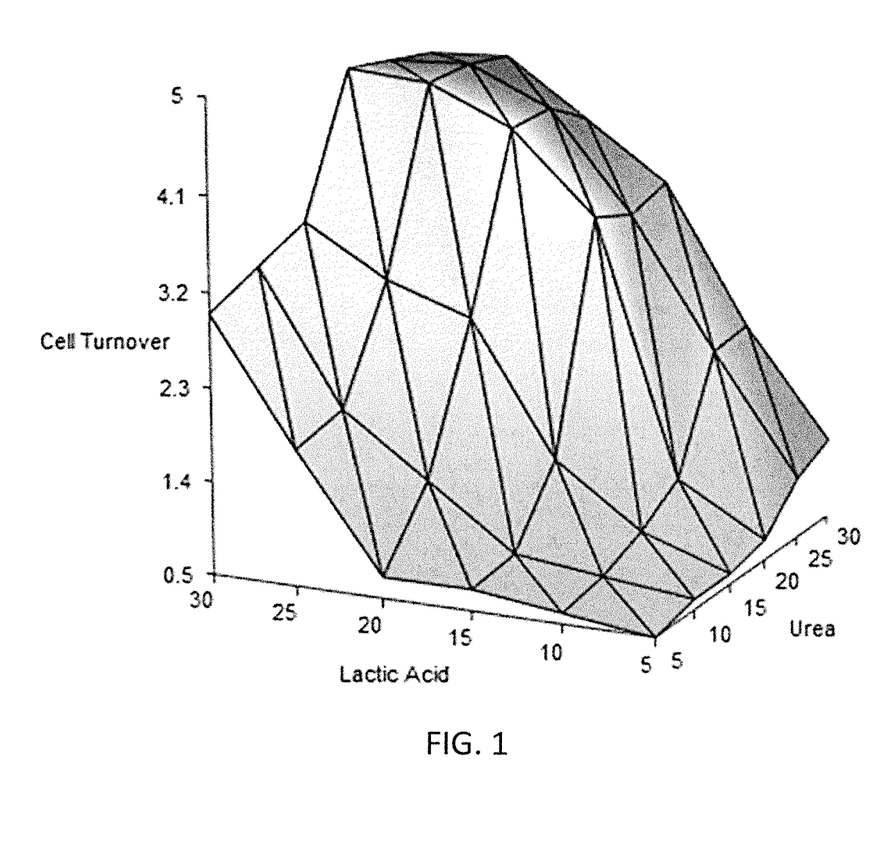
FIG. 1 illustrates exfoliation using a variety of systems with differing amounts of lactic acid (X axis, shown in weight percent) and urea (y axis, shown in weight percent) when used as a first phase and combined with use of a second phase including triethanolamine as an exemplary neutralizer.
Figure 2:
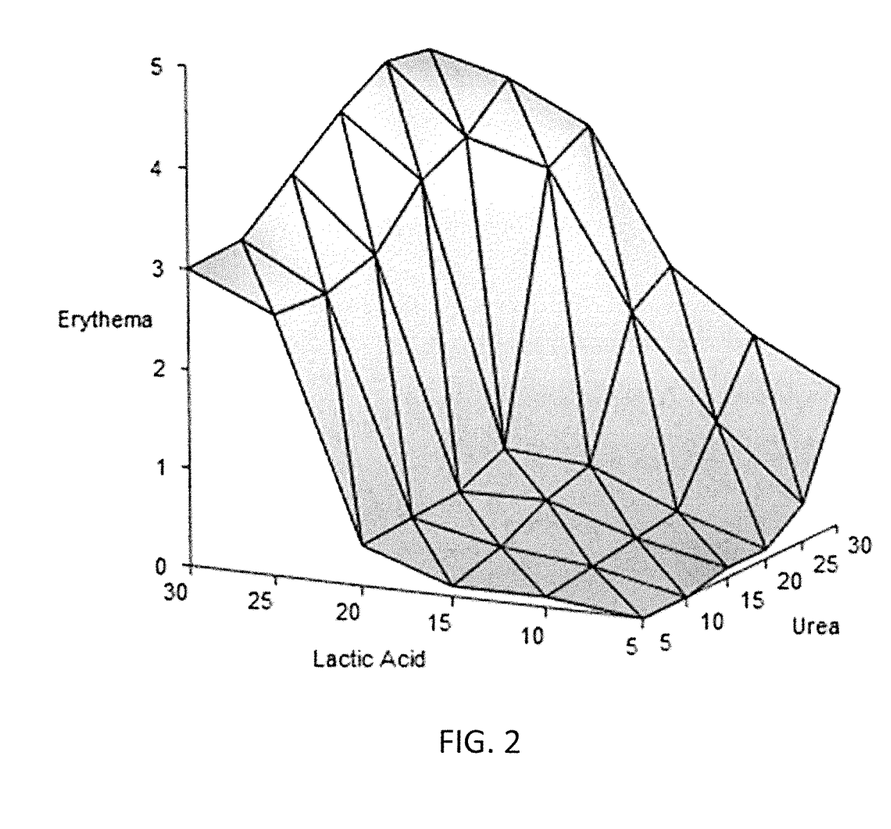
FIG. 2 illustrates erythema using a variety of systems with differing amounts of lactic acid (X axis, shown in weight percent) and urea (y axis, shown in weight percent) and combined with use of a second phase including triethanolamine as an exemplary neutralizer.

Each of the tested systems show increased rates of skin cell turnover as measured by both the dansyl chloride method and the forced exfoliation method by 10% to 80% as illustrated in Table 1 demonstrating the dansyl chloride method results. Results for the dansyl chloride method are also illustrated in FIG. 1 that clearly demonstrates above 15% wt lactic acid and above 10% wt urea combined results in a rapid increase in efficacy that begins to peak at 20% wt of both lactic acid and urea. Little increase in efficacy is observed beyond 20% wt of either lactic or urea.

TABLE 4

Effect of varying concentrations of lactic acid and urea on cell turnover presented on a relative scale from 0-5 with zero being no observed turnover and 5 being the most observed turnover.

| Urea (wt %) | Lactic Acid (wt %) | Cell Turnover |
|---|---|---|
| 5 | 5 | 0.5 |
| 5 | 10 | 0.6 |
| 5 | 15 | 0.7 |
| 5 | 20 | 0.7 |
| 5 | 25 | 1.8 |
| 5 | 30 | 3.0 |
| 10 | 5 | 0.6 |
| 10 | 10 | 0.7 |
| 10 | 15 | 0.8 |
| 10 | 20 | 1.4 |
| 10 | 25 | 2.0 |
| 10 | 30 | 3.3 |
| 15 | 5 | 0.6 |
| 15 | 10 | 0.9 |
| 15 | 15 | 1.5 |
| 15 | 20 | 2.8 |
| 15 | 25 | 3.1 |
| 15 | 30 | 3.6 |
| 20 | 5 | 0.7 |
| 20 | 10 | 1.2 |
| 20 | 15 | 3.7 |
| 20 | 20 | 4.5 |
| 20 | 25 | 4.9 |
| 20 | 30 | 5.0 |
| 25 | 5 | 1.1 |
| 25 | 10 | 2.3 |
| 25 | 15 | 3.6 |
| 25 | 20 | 4.6 |
| 25 | 25 | 5.0 |
| 25 | 30 | 5.0+ |
| 30 | 5 | 1.3 |
| 30 | 10 | 2.4 |
| 30 | 15 | 3.8 |
| 30 | 20 | 4.4 |
| 30 | 25 | 5.0 |
| 30 | 30 | 5.0+ |

Example 3

Each of the formulas of Example 2 are also tested for irritation on human skin in 28 volunteers. A pain response (stinging) test is performed by applying the systems to the nasolabial fold region. This test site is highly innervated with sensory fibers. The pain response test is an established method for interrogating dermatological substances for their propensity to induce irritation. As a control, saline solution is applied in equal volume to the contralateral test site. The systems are allowed to incubate on the skin for 1 minute and an overall pain response is recorded on a scale of 1 to 5 with 1 equating to no increase in pain or other sensitivity relative to control side, and 5 equating to severe pain or other sensitivity relative to control.

The irritation of the tested systems are further assessed using a Chroma Meter (Konica Minolta). Two test sites are chosen on the cheeks of 28 human volunteers for testing of a test composition or saline control. Each test site is approximately 3 centimeters in area. For each test site, 1 ml of the systems of Example 2 or saline is applied to the test site and allowed to absorb for 20 minutes. The degree of redness is measured using the Chroma Meter at the test and control sites 25 minutes after application. The results illustrate very little irritation at concentrations of either lactic acid or urea at or below 20 weight percent. If 20 weight percent lactic acid is exceeded the amount of irritation increases dramatically. Similar results are demonstrated with amounts in excess of 20 weight percent urea. A notable low level of irritation is observed at 20 weight percent lactic acid and 20 weight percent urea when combined. Comparing this amount of irritation with the efficacy of Example 2 and FIG. 1 illustrates that excellent and very high levels of efficacy are achieved at excess of 15 weight percent lactic acid and excess of 15 weight percent urea with these amounts also producing very low levels of irritancy.

TABLE 5

Irritancy of varying concentrations of lactic acid and urea on cell turnover presented on a relative scale from 0-5 with zero being no change in skin redness (marker of irritancy) and 5 being the most observed redness.

| Urea (wt %) | Lactic Acid (wt %) | Erythema |
|---|---|---|
| 5 | 5 | 0.0 |
| 5 | 10 | 0.1 |
| 5 | 15 | 0.1 |
| 5 | 20 | 0.4 |
| 5 | 25 | 2.6 |
| 5 | 30 | 3.0 |
| 10 | 5 | 0.0 |
| 10 | 10 | 0.2 |
| 10 | 15 | 0.3 |
| 10 | 20 | 0.5 |
| 10 | 25 | 2.7 |
| 10 | 30 | 3.2 |
| 15 | 5 | 0.1 |
| 15 | 10 | 0.3 |
| 15 | 15 | 0.6 |
| 15 | 20 | 0.6 |
| 15 | 25 | 3.0 |
| 15 | 30 | 3.8 |
| 20 | 5 | 0.1 |
| 20 | 10 | 0.4 |
| 20 | 15 | 0.8 |
| 20 | 20 | 0.9 |
| 20 | 25 | 3.7 |
| 20 | 30 | 4.4 |
| 25 | 5 | 0.4 |
| 25 | 10 | 1.2 |
| 25 | 15 | 2.3 |
| 25 | 20 | 3.8 |
| 25 | 25 | 4.1 |
| 25 | 30 | 4.9 |
| 30 | 5 | 1.5 |
| 30 | 10 | 2.0 |
| 30 | 15 | 2.7 |
| 30 | 20 | 4.2 |
| 30 | 25 | 4.7 |
| 30 | 30 | 5.0+ |

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified. Methods of nucleotide amplification, cell transfection, and protein expression and purification are similarly within the level of skill in the art.

Patents and publications mentioned in the specification are indicative of the levels of those skilled in the art to which the invention pertains. Each patent, application or publication is incorporated herein by reference to the same extent as if each individual patent, application or publication was specifically and individually stated as incorporated herein by reference for the specific teaching for with each reference is cited and additionally for entirety of their contents including text, figures, and references. Citation of any document is not to be construed as an admission that it is prior art with respect to the present invention.

The foregoing description is illustrative of particular aspects of the invention, but is not meant to be a limitation upon the practice thereof.

What is claimed is:

1. A system for enhancing skin renewal, comprising:
   (a) a first phase, the first phase substantially excluding water, and the first phase comprising:
      (i) an anhydrous solvent;
      (ii) a hydroxy acid; and
      (iii) urea; and
   (b) a second phase comprising a neutralizing agent.

2. The system of claim 1, wherein the hydroxy acid is selected from the group consisting of alpha hydroxy acid, beta hydroxy acid, gamma hydroxy acid, and combinations thereof.

3. The system of claim 2, wherein the alpha hydroxy acid is selected from the group consisting of malic acid, lactic acid, glycolic acid, citric acid, and combinations thereof, and wherein the beta hydroxy acid is selected from the group consisting of salicylic acid, acetylsalicylic acid, and combinations thereof.

4. The system of claim 1, wherein the hydroxy acid and the urea are each present in the first phase at a concentration of from 8% to 25% by weight.

5. The system of claim 1, wherein a ratio of hydroxy acid to urea in the first phase is from 2:1 to 1:2.

6. The system of claim 1, wherein the neutralizing agent selected from the group consisting of sodium hydroxide, potassium hydroxide, triethanolamine, ammonium hydroxide, tris(2-aminoethyl)amine, and combinations thereof.

7. The system of claim 1, wherein the second phase further comprises an abrasive agent selected from the group consisting of polyethylene granules, silica particles, hydrated silica particles, and combinations thereof.

8. The system of claim 1, wherein the first phase, the second phase, or both the first phase and the second phase further comprises at least one bioactive agent.

9. The system of claim 8, wherein the at least one bioactive agent is selected from the group consisting of vitamin A, a derivative of vitamin A, vitamin E, a derivative of vitamin E, an anti-infective agent, and combinations thereof.

10. The system of claim 1, wherein the first phase and the second phase are each independently provided in a form selected from the group consisting of a lotion, a cream, a gel, a bar, an ointment, an impregnated pad, and a liquid.

11. A package comprising the system of claim 10.

12. A composition for enhancing skin renewal, comprising:
   (a) a first phase, the first phase substantially excluding water, and the first phase comprising:
      (i) glycerin;
      (ii) lactic acid; and
      (iii) urea; and
   (b) a second phase comprising:
      (i) triethanolamine; and
      (ii) hydrated silica beads,
   wherein the first phase and the second phase are intermixed upon topical application to a skin treatment surface.

13. The composition of claim 12, wherein the first phase comprises: from 50% to 80% by weight glycerin; from 10% to 25% by weight lactic acid; and from 10% to 25% by weight urea.

14. The system of claim 1, wherein the first phase is comprised of less than or equal to 2% by weight water.

15. The composition of claim 12, wherein the first phase is comprised of less than or equal to 2% by weight water.

* * * * *